United States Patent [19]

Gombocz et al.

[11] Patent Number: 5,275,710
[45] Date of Patent: Jan. 4, 1994

[54] GEL ELECTROPHORESIS SYSTEM INCLUDING OPTICAL STAGE, SAMPLE APPLICATOR AND SAMPLE RETRIEVER

[75] Inventor: Erich A. Gombocz, Menlo Park; Alex T. Roth, Foster City, both of CA.

[73] Assignee: Labintelligence, Inc., Menlo Park, Calif.

[21] Appl. No.: 837,067

[22] Filed: Feb. 14, 1992

Related U.S. Application Data

[63] Continuation-in-part of Ser. No. 522,325, May 14, 1990, Pat. No. 5,104,512, and a continuation-in-part of Ser. No. 772,947, Oct. 8, 1991.

[51] Int. Cl.$^5$ .............. G01N 27/26; G01N 27/447; B01D 57/02
[52] U.S. Cl. .............. 204/299 R; 204/182.8
[58] Field of Search .............. 204/299 182.8, 182.7, 182.9, 180.1

[56] References Cited

U.S. PATENT DOCUMENTS

| | | | |
|---|---|---|---|
| 3,428,547 | 2/1969 | Zec | 204/182.7 X |
| 3,495,446 | 2/1970 | Williamson | 204/182.7 X |
| 3,839,183 | 10/1974 | Klein et al. | 204/299 R |
| 3,932,229 | 1/1976 | Grandine | 204/299 R X |
| 4,004,548 | 1/1977 | Smola et al. | 204/299 R X |
| 4,214,973 | 7/1980 | Nakamura | 204/182.7 X |
| 4,414,073 | 11/1983 | Iwata et al. | 204/182.8 X |
| 5,139,637 | 8/1992 | MacConnell | 204/182.8 X |

OTHER PUBLICATIONS

Anthony T. Andrews "Electrophoresis: Theory, Techniques, and Biochemical, and Clinical Applications, 2nd edition" p. 79.

Primary Examiner—John Niebling
Assistant Examiner—John S. Starsiak, Jr.
Attorney, Agent, or Firm—Bertram I. Rowland

[57] ABSTRACT

An electrophoretic system is provided which allows for carrying out electrophoresis while monitoring and regulating the temperature and the electrical field gradient in the gel. In addition, photometric monitoring, including use of an optical stage, is provided so as to monitor the progress of the electrophoretic separation and vary conditions to change the progress as desired. A computer is employed which receives the signals from the electrophoretic and photometric apparatuses and regulates temperature and voltage to either maintain conditions, or change the conditions to vary the progress of the electrophoresis and to store the separation results. A sample applicator and a sample retriever are also provided, to provide even and consistent application of sample to the gel and to allow recovery of portions of the sample without destroying or removing pieces from the gel. Gel molds are provided for forming the lanes in a gel plate, as well as a light module, for reading the bands present in the gel lanes with the photometer.

26 Claims, 11 Drawing Sheets

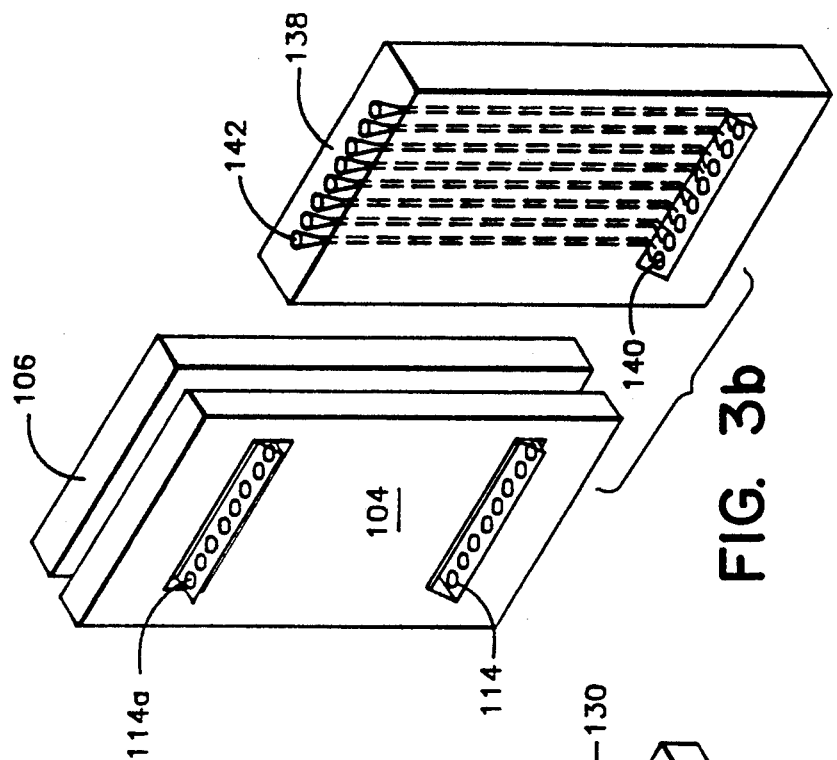
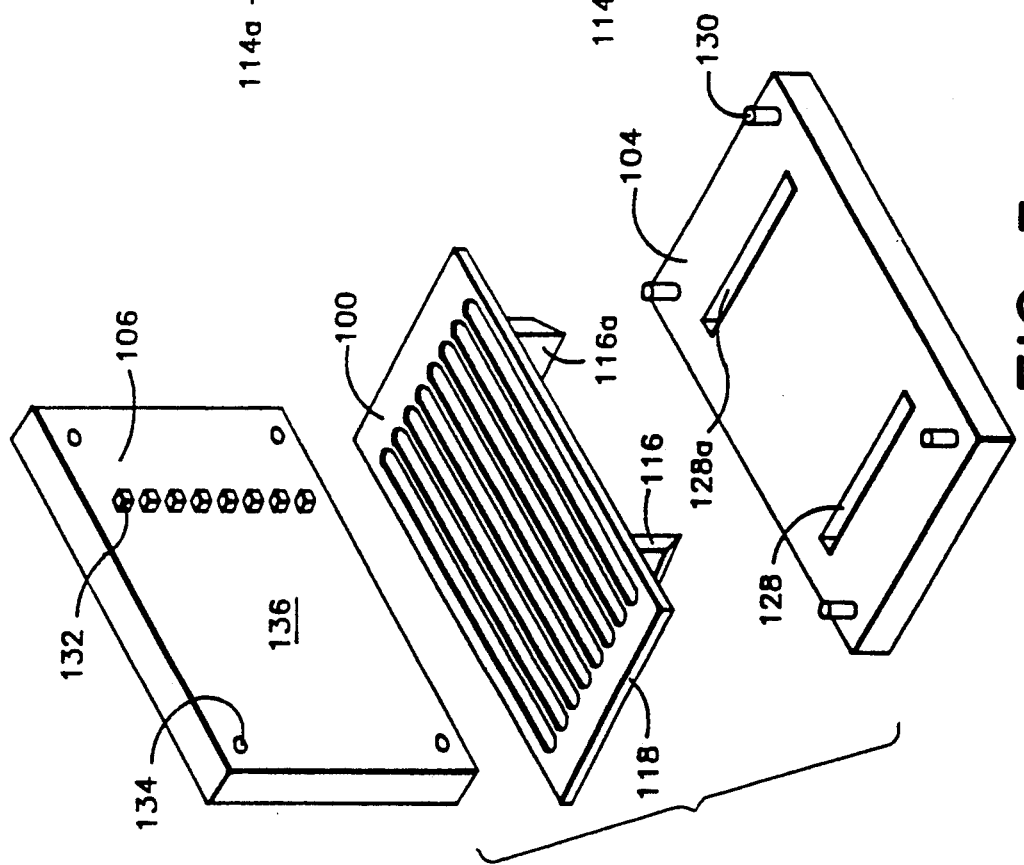
FIG. 3b
FIG. 3a

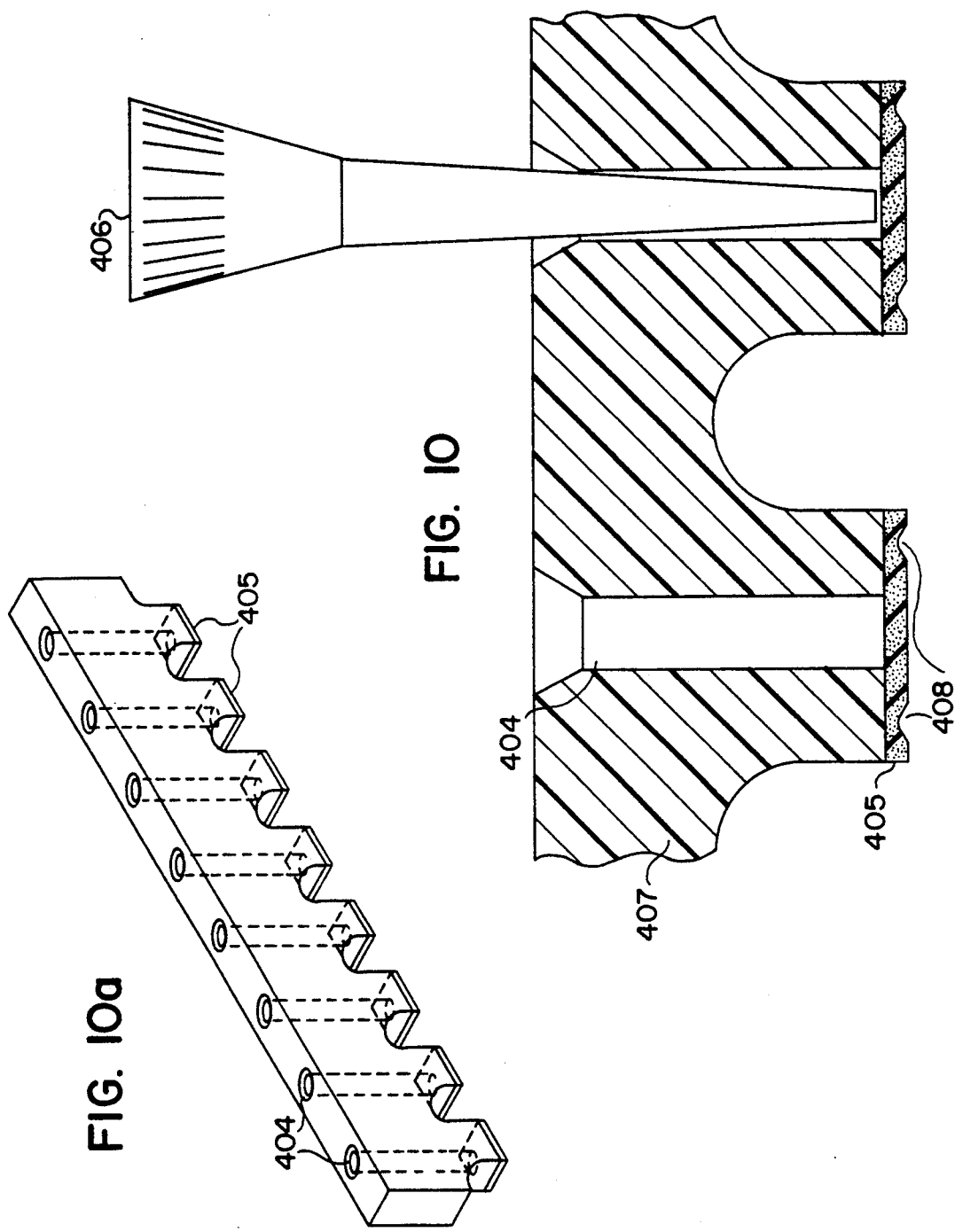

GEL ELECTROPHORESIS SYSTEM INCLUDING OPTICAL STAGE, SAMPLE APPLICATOR AND SAMPLE RETRIEVER

CROSS-REFERENCE TO RELATED APPLICATIONS

This application is a continuation-in-part of U.S. patent application Ser. No. 07/522,325, filed May 14, 1990 and U.S. patent application Ser. No. 07/772,947, filed Oct. 8, 1991.

INTRODUCTION

1. Technical Field

The field of this invention is gel electrophoresis.

2. Background

With the huge expansion in biotechnology, gel electrophoresis has become an indispensable tool. The ability to separate nucleic acid fragments and proteins by means of size, shape and charge has added numerous opportunities to identify specific compounds, indicate purity, and allow for isolation of a compound in relatively pure form. By being able to change the conditions under which one carries out the electrophoresis, one can determine many characteristics of the compounds in the sample.

A variety of new techniques are predicated on the use of gel electrophoresis in an efficient and convenient way. Restriction fragment length polymorphisms is one application where one can perform genetic diagnosis by means of a genomic DNA sample. This technique may also be used in forensic medicine to identify the source of nucleic acids. Gel electrophoresis may also be used to identify a compound, by separation of a complex mixture and then by using markers,, such as antibodies, or the like. Electrophoresis is used in conjunction with transfer to a membrane such as Southern, Northern, and Western blotting, or other techniques involving transfer of the separated sample to a different substrate.

While much of the power of gel electrophoresis as a tool in identification and separation is realized, there are still many shortcomings. Apparatuses tend to be relatively large and cumbersome. Comparisons from samples or runs and particularly from different laboratories are very difficult since conditions of the electrophoresis vary and regulation and monitoring of the conditions is not available or unreliable. Thus, one frequently gets wide variation in determinations of molecular weight, as well as the properties of the sample components. Therefore, it has been very difficult to make comparisons from one run to another, no less from one laboratory to another.

Additionally, the gel electrophoretic apparatus usually does not prevent the sample from running off the gel, nor does it provide assurance that the sample has had sufficient time for a reasonable separation. Thus, substantial improvements in presently available equipment is desirable in order to obtain a satisfactory electrophoretic separation.

There is substantial interest in being able to provide electrophoretic systems which can be substantially automated, assure directly comparative results, and provide economies in the use of electrophoresis.

Relevant Literature

References include Schafer-Nielsen, *Electrophoresis* 1987, 8, 20; Szewaczyk et al., *ibid* 1987, 8, 25; Gill *et al., ibid* 1987, 8, 38; Demeulemester *et al., ibid* 1987, 8, 71; Blum, *et al., ibid* 1987, 8, 93; Albaugh *et al., ibid* 1987, 8, 140; Serwer and Hayes, *ibid* 1987, 8, 244; Zapolski *et al., ibid* 1987, 8, 255; Tietz *et al., ibid* 1987, 8, 271; Breborowicz *et al., ibid* 1987, 8, 313; Pascali *et al., ibid* 1987, 8, 371; Orban *et al., ibid* 1987, 8, 465; Frey *et al., ibid* 1986, 7, 28; Carpenter *et al., ibid* 1986, 7, 221; Tietz *et al., ibid* 1986, 7, 241; Lamben *et al., ibid* 1986, 7, 342; Foret *et al., ibid* 1986, 7, 430; Prin *et al., ibid* 1985, 6, 268; Lockshin, *ibid* 1985, 6, 282; Mosher and Thormann, *ibid* 1985, 6, b/77; Rhalem and Pery, *ibid* 1985, 6, 564.

SUMMARY OF THE INVENTION

A gel electrophoresis system is provided comprising a gel electrophoresis apparatus having a gel slab supporting platform, an optical stage, buffer wells, electrodes for maintaining an electrical field across the gel, a pair of electrodes to monitor the voltage in the gel, and temperature monitoring and controlling means for controlling the temperature in the gel. Also provided is a stacking gel in a portion of the gel platform to concentrate fractions present in the sample. In addition, the system includes a sample applicator, a sample retriever, and a gel holder and forms for preparing gels, particularly as a plurality of individual lanes.

An improvement over gel systems currently in use is disclosed wherein the support platform or gel tray may be fashioned to allow the preparation of a stacking gel through which ions contacting the sample will migrate before reaching the separation gel. This improvement allows sharper focusing of the sample before separation, and better resolution of individual portions of the sample upon separation.

Ancillary to the separation gel slab is a spectrophotometer means for monitoring the movement of fractions in the gel. Another substantial improvement for a gel monitoring system is disclosure of an optical stage, which allows gel monitoring with UV and visible light and combinations of these spectra by use of UV transmitting glass backed with a spectral coating.

An improvement is also provided in the form of a sample applicator to allow easy and reproducible application of the sample into the gel lane.

Another improvement disclosed is a sample retriever, whereby individual portions of samples subjected to gel electrophoresis may be isolated and recovered intact from the gel without the necessity of destroying the gel or use of complicated recovery procedures.

The progress of an electrophoresis is monitored as to temperature of the gel, electrical gradient across the gel, progress of individual bands and the separation between bands by UV and visible light monitoring, where a constant temperature and field may be maintained or varied depending upon the purpose of the electrophoresis.

The system provides for accurate reproducible separation of nucleic acids, proteins, saccharides, particles, such as virus particles, and determination of the size and characteristics of individual molecules and particles.

DESCRIPTION OF THE DRAWINGS

FIG. 3a and 3b are diagrammatic perspective view of the gel casting components.

FIGS. 9a1 and 9a2 are a perspective view of the upper light stage assembly, also showing the spectrum profile of a spectral coating;

FIG. 10 and 10a are a perspective view of the sample applicator, with a cross section to show the wick and application mode.

DESCRIPTION OF THE SPECIFIC EMBODIMENTS

Figure 1:
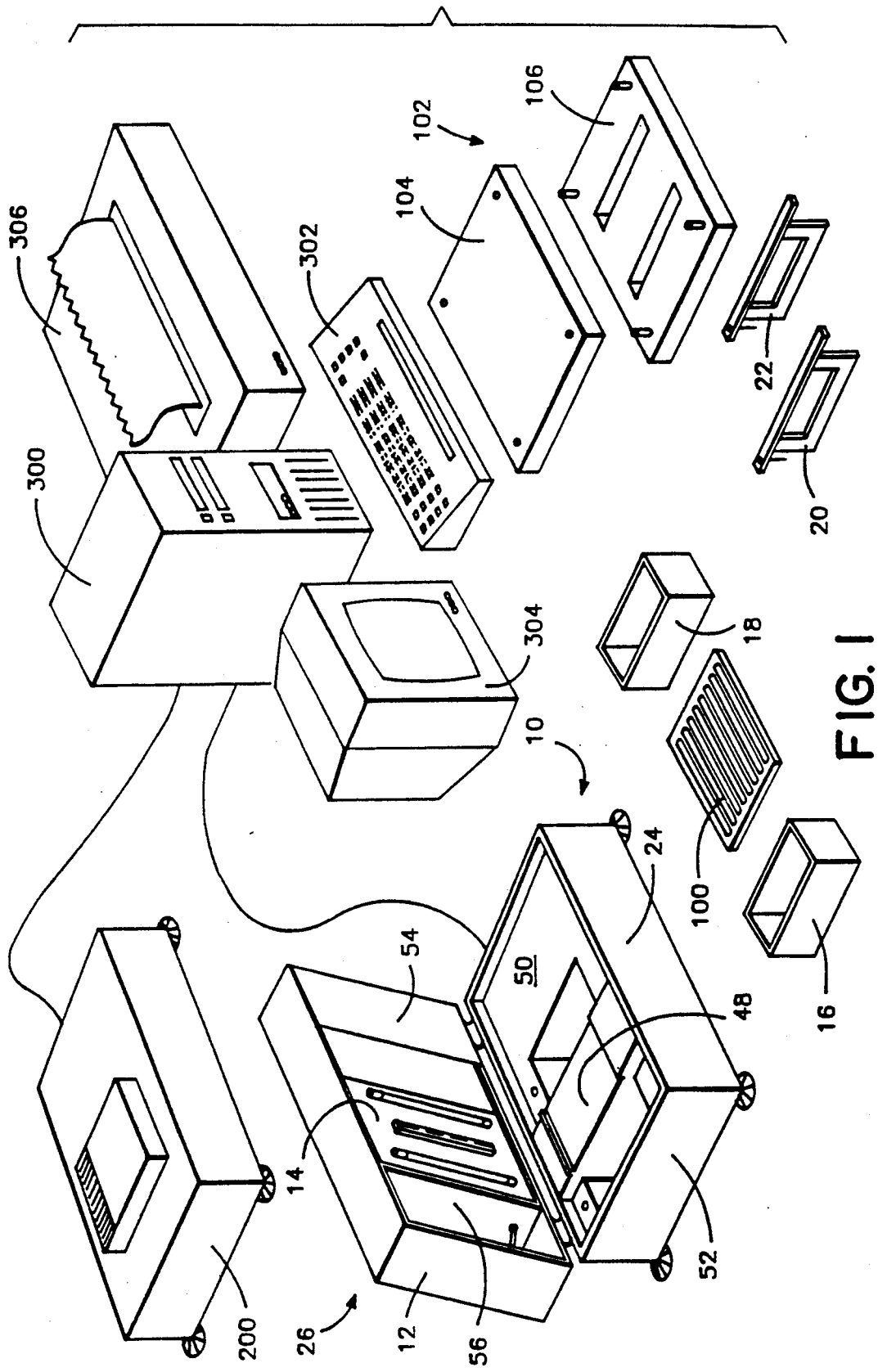
FIG. 1 is a diagrammatic representation of the electrophoresis system according to this invention.

An integrated gel electrophoresis system is provided which allows for controlled reproducible separation of macromolecules, including nucleic acids, proteins, saccharides, and combinations thereof. The system provides for monitoring and regulating a number of variables associated with the gel electrophoresis. By monitoring the status of each of a plurality of variables associated with the gel electrophoresis and regulating the conditions of the gel electrophoresis, reproducible band patterns can be achieved, and conditions standardized or varied depending upon the particular needs of the electrophoresis.

Among the variables monitored are the voltage gradient in the gel, the temperature of the gel, and the movement of one or more bands in the gel. By insuring a stable temperature and electrical field in the gel, the molecules in the sample move in a reproducible manner through the gel.

In an improved method for separation of sample components described herein, the effect of denaturation on protein components is used to isolate components in a sample. Thus, by allowing the temperature resulting from the heat generated in the gel by the electrical current or field to be programmed by a controlled rate of cooling, proteins will be denatured at different times in relation to the temperature increase. Consequently, the relative mobility ($R_f$) of the component increases, slowing and often stopping the progress of that component in the gel.

By monitoring the progress of the movement of the sample bands using UV, visible or other light source provided with this invention, one can increase or decrease the voltage gradient in the field to increase or decrease the rate of movement of the molecules or terminate the electrophoresis, when a desired level of separation or desired distance traveled has been obtained.

By providing for a temperature control platform, in the form of a thermal stage to support the gel and optionally an optical stage, and providing for good heat transfer between the platform and the gel, the temperature in the gel may be maintained within a relatively narrow range. One or more temperature sensors, e.g., thermocouples or integrated circuit temperature sensors, may be employed so as to monitor the temperature with the temperature control platform, at the surface of the thermal stage and/or in the gel, so that information may be continuously fed to a monitor for regulating the temperature in the gel. In this way the temperature may be accurately held within a narrow range or programmed to rise in accordance with a predetermined schedule, where the temperature and time are recorded.

The voltage gradient in the gel may be monitored by having two or more electrodes distinct from the electrodes which provide the voltage gradient across the gel. These additional electrodes would be spaced apart across a substantial portion of the gel, usually greater than about 60%, preferably 70%, of the length of the gel. The electrodes would be in contact with the gel, conveniently at an edge, so as to be able to determine the voltage drop between the two electrodes and across the gel in the direction of the field. By monitoring the actual voltage in the gel, variations in the field in the gel may be regulated to maintain a constant field. By maintaining a constant field and a constant temperature, the significant conditions controlling the movement of molecules in the gel can be maintained, so that the molecules move in a regulated and reproducible fashion.

Thus, in a preferred embodiment there will be functional connection between the light source monitoring of the gel and the temperature control monitoring of the gel. For example, bands in the gel may be electrophoresed to a predetermined point along the length of the gel, and at that point the temperature will be allowed to or made to rise, initiating a "second stage" separation or isolation by denaturation.

The separation path length may start at the sample application position. The separation distance is usually at least about 5 cm, preferably at least about 10 cm, which is about 75% of the total gel distance. The remaining portion of the gel, from the catholyte to the sample application position, will be available for stacking, unless stacking is obtained by another method.

The progress of the electrophoresis is monitored, so that the progress of the bands is determined. The progress is monitored spectrophotometrically, where the absorption or fluorescence of the molecules, normally resulting from staining of the molecules present in the gel, may be determined. Detection of the bands may be as a result of endogenous spectrophotometric properties of the molecules or as a result of the presence of dyes or label conjugates in the gel or band which may interact with the molecules to provide for variation in spectrophotometric properties associated with the presence of the molecules in the gel. Thus, the progress of the bands in the gel may be monitored by irradiation with light, e.g., UV or visible light.

During the course of the electrophoresis, opportunities exist to vary conditions, such as temperature and electrical field gradient, to reduce or increase the rate of movement of the molecules in the gel. Thus, one can increase or decrease the rate at which the electrophoresis is carried out or stop the electrophoresis as desired, by modulating the current or by allowing the heat to increase to denaturation levels. Rather than having to wait until a marker has moved to some predetermined position on the gel or has gone off the gel, one can terminate the electrophoresis at any appropriate time.

The repetitive monitoring of temperature and electrical field in conjunction with monitoring of the progress of the electrophoresis, with concurrent regulation of temperature and electrical field, provides the capability of reproducibly controlling the conditions under which the electrophoresis is carried out. By providing comparable conditions with a comparable apparatus, one can be assured that comparable results will be obtained, whether at the same laboratory or different laboratory. The significance of being able to compare results means that one can have greater certainty whether the same or different materials are involved, as well as the significance of the characteristics of the sample which are determined from the electrophoresis.

By monitoring the variables associated with the electrophoresis, numerous other additional advantages are achievable. For example, one can use soft gels which allow for relatively rapid migration of sample components, since the movement of the components may be monitored. Additionally, by selecting a soft gel for separation and providing for programmed heat increase to denaturing levels, protein components may be isolated from very narrow, distinct zones in the gel in relation to the distance they have traveled prior to denaturation. In this way, very large particles and molecules may be separated and characterized.

One may also provide for Ferguson plots, by having a plurality of lanes at different gel concentrations resulting in different pore sizes of the gel matrix. The reproducibility of the plot allows for comparison between components in different samples and provides an additional characteristic for identification of a particular composition or molecule. Other advantages will also be apparent as the system is described further.

The system comprises the gel module which has a temperature regulated platform on which the gel plate sits, buffer well containers which may be fixed or removable, and electrodes, which may be fixed or removable for placing in the buffer wells to provide the electrical field in the gel.

The gel plate is formed essentially of a horizontal support for a gel and vertical support means, which include open channels for the flow of buffer or electrolyte solutions or for the formation of portions of the gel, i.e., a stacking gel or a separating gel. Orifices connecting with the channels running through the length of the vertical support means at the surface of the horizontal support provide for connection between the gel in the channel and the gel on the support. These channels are part of a current path from electrodes in the buffer tanks through the solution or composition, normally gel composition, present in the vertical support, through the horizontal gel and the composition in the other vertical support, the electrolyte buffer and the other electrode.

A substantial improvement over currently used gel modules is the ability to form a stacking gel in one portion of the gel plate apparatus. A stacking portion of a gel is formed using a buffer of ions which run more quickly through gel than do the ions in the buffer forming the separation portion of the gel. Thus, leading ions moving through the stacking portion define the ion concentration in the trailing ions, which in the gel system are represented by charged portions of the sample and any dyes running with the sample. This "definition" causes a sharpening of the components of the sample prior to separation, such that well-defined bands are formed in the separation gel.

In the current embodiment, the stacking gel may be formed in a column in the vertical support means of the gel plate, such that the leading ions in the stacking gel pass through the sample application site and can align the components of the sample prior to their entering the separation gel to provide for sharper bands. The stacking gel may be prepared to end and abut the separation gel at or about the orifice where the vertical support meets the horizontal gel plate. Optionally, the stacking gel may be prepared so that it ends and abuts the separation gel on the horizontal gel plate, at or beyond the area of sample application, usually in proximity to the site, less than about 10% of the total distance of the separation gel.

In one embodiment, the entire gel is formed of "stacking buffer" and a gel with a very low matrix composition (i.e., about 5–7.5% where the gel is acrylamide, or about 0.2–0.5% where the gel is agarose) is formed. In this way, large sample molecules are focussed into sharp bands by denaturing conditions, as described above.

The concentration of ions in the stacking buffer gel will be selected in accordance with the composition of the separation buffer gel. Thus, the buffer selected for the stacking gel will vary with the experiment. Buffers will be selected primarily by consulting the extensive literature in this area, for example, *The Practice of Quantitative Gel Electrophoresis* (Advanced Methods in the Biological Sciences series); Andreas Chrambach, VCH Publishers, (1985), incorporated herein by reference.

The gel module has a pair of electrodes for fitting into the gel holder and determining the electrical field gradient in the gel. In addition the gel module has electrical connections for powering the thermal system and electrodes for producing the electrical field gradient in the gel and connecting the thermal system, the field gradient electrodes and the gel monitoring electrodes to a monitoring and regulating means for controlling the variables associated with the temperature and electrical field in the gel. Thus, by monitoring the temperature of the gel, the thermal plate may be regulated to allow for programmed heating of the gel, so that separation of components by size and charge may by complemented with separation by an additional separation under denaturing conditions.

Another improvement over gel systems currently in use is the provision of an optical stage positionable upon the thermal stage of the temperature control platform. This stage forms part of the separation monitoring means. This optical stage consists of a platform of UV- and visible light-transparent material, preferably of glass. The stage is positioned under the gel tray. The stage may extend for most of the length or width of the gel, although stages smaller than the gel in length or width may be useful for different applications.

The optical stage will be coated or prepared on one side with a spectral coating. The coating or preparation selected will be UV-reflective, at the same time being substantially visible-light transparent. This allows monitoring of the progress of the sample in the gel by use of at least three different wavelength ranges of light: UV, visible, and combinations of portions of all these spectra.

Thus, the sample may be detected as a result of inherent spectrophotometric properties of the molecules. Alternatively or additionally, the sample or gel may be treated with dyes or other materials well known in the art rendering portions of the sample visible under U.V. or visible light or both.

In a preferred embodiment, the optical stage may be positioned such that U.V. light is transmitted through the gel and samples therein, impinges upon the spectral coating and is reflected back through the gel and sample to provide optimal illumination of the sample components separated by the gel. The sample may also be illuminated with visible light. The optical stage makes it possible that the gel and sample therein be illuminated from below the gel, since the spectral coating allows substantial transmission of visible light. Thus, in a presently preferred embodiment, the gel will be illuminated with visible light from below the gel and with U.V. light from above the gel. When light is transmitted through the gel, light absorption by bands may be measured.

A removable backlit plate may be provided for mounting on the thermal stage, which would allow for reading the gel, after the electrophoresis has been finished and the gel stained or the nucleic acid labeled.

Removably mounted on the gel module is a photometer module, which provides an excitation light source and a spectrophotometer which detects zone fluorescence or light absorption in the gel. Controlled motor-driven mechanical means are provided for moving the spectrophotometer and excitation light source over the surface of the gel to scan the gel. The light measure in relation to the bands in the gel, when irradiated by either the photometer module light source or a source below the gel, is detected and the resulting signal transmitted to the monitoring and regulating means for controlling the progress of the electrophoresis. Means are provided for locating the position of the photometer module in relation to the gel at any time.

In addition, a light box may be provided over which the photometer module fits, where the gel holder may be scanned spectrophotometrically for light absorption or emission. The light box may be in addition to or in lieu of an electroluminescent panel.

The monitoring and regulating means is conveniently a computer with appropriate software for regulating the conditions and progress of the electrophoresis. Optionally included will be a keyboard for interacting with the computer and a monitor for visually monitoring the conditions and progress of the electrophoresis.

For convenience, gel molds and plates for holding the gel are provided, where the gel plates are designed for accommodation with the gel platform and buffer wells and for receiving the monitoring electrodes.

In another embodiment, a sample applicator is provided to allow precise and controlled application of a sample in liquid form to the gel. Sample may be introduced into the applicator housing via an applicator channel or passageway which extends through the housing. The applicator itself will preferably be formed of a transparent material to simplify the loading of sample. The bottom or lower opening of each applicator channel is covered by an absorbent material, e.g. wick, which prevents sample from uninhibited flow onto the gel. The wick is selected to hold a measured amount of sample, and thus the sample is applied in a predetermined amount to the gel when the wick is contacted with the gel and a current is applied.

The wick can be of any convenient absorbent material, such as spun fabric, plastic, fiberglass, sponge, paper or similar material, of a measured size to hold a specific amount. When the applicator is lowered onto the gel so that the wick(s) contacts the gel, the sample will quite easily and consistently be electrophoresed from the wicks. Wicks may be held to the applicator by a variety of means, such as heat fusion, adhesives, staples, pins and the like.

The sample applicator may have a single channel or up to a plurality of channels equal to the number of lanes in the gel. The channels will have volumes in the range of about 10 to 50 $\mu$l, usually about 10 to 20 $\mu$l. The channel may be cylindrical, conical or other convenient shape.

In conjunction with the sample applicator, a sample concentrator may be employed, as described in U.S. patent application Ser. no. 07/522,325, filed May 14, 1990, now U.S. Pat. No. 5,104,512. See, FIG. 6. The electrophoretic concentrator provides a chamber, conveniently in the shape of a cone, having a stacking gel at the lower portion of the chamber with a passage which terminates in an opening for transferring the concentrated sample to the sample applicator. The volume of the sample in the chamber will usually be in the range of about 0.5 to 10 ml, while the chamber will have a volume of up to 25 ml. The opening may be in contact with the wick or with a small amount of liquid at the bottom of the chamber to provide for passage of electrical current. By having a block with a plurality of chambers, each with a common stacking gel, each of the wicks will receive a sample simultaneously. Alternatively, one may have different stacking gels and/or different buffers where the concentration times will be different.

An electrode is provided proximal to the top of the chamber for providing a voltage gradient between such electrode and an electrode in the gel to provide a voltage gradient for stacking of the sample and transferring the concentrated sample to the wick. By the appropriate choice of the buffer ions, one may select the nature of the components in the gel which will be concentrated and transferred to the wick. Thus, a highly concentrated sample is transferred to the gel to provide for better resolution.

In another embodiment, a sample retriever is provided, with which individual portions of a sample subjected to gel electrophoresis may be isolated and recovered from the gel, without the necessity of destroying the gel or use of complicated recovery procedures. An electrode or series of individually regulatable electrodes are employed, positioned so as to be in contact with one or more electroconductive media in the channels or passageways of the retriever, held in said channel by an absorbent matrix. The electrode may be at the top of the channels, extend downward into the channels or penetrate through the walls of the channels for electrical contact with the media. The particular placement of the electrode is not critical to this invention. The electroconductive media can be semisolid compositions or gels or absorbent matrices wetted with a conductive medium. The media are in contact with an absorbent material, e.g. wick, at the lower end of the channel. The sample retriever may be placed onto a gel from which a portion of a sample is to be recovered such that a wick is in electrical contact with the gel at the band comprising the portion. By passing a current between the retriever electrode and one other electrode on the opposite side of the band, the sample portion may be moved into the electroconductive medium in the retriever channel and removed through an upper opening. The sample retriever may have a similar structure to the applicator.

The electroconductive media matrix in the channels holds the media in the channels. The matrix may be formed of a wide variety of materials such as fiber, paper, sponge, gel or any number of such materials that will absorb a conductive, e.g. aqueous, media in the channels.

Modifications to this embodiment may be made to enhance different aspects of the sample retriever. For example, the electrode of the retriever can be designed to function over individually selected lanes or groups of lanes of a gel. Thus, the retriever may be programmable with the apparatus described herein to respond to the progress of different bands in individual gel lanes. A selected band may be retrieved simply by charging one member of the individually regulatable electrodes over the lane in which it is running, leaving the rest of the lane and the gel intact for further electrophoresis. Similarly, this retriever may be used to apply reagents to the gel, by reversing the current flow, such that individual components of the sample running in the gel will be stained, visualized, reacted or the like.

Turning now to the drawings, FIG. 1 is a diagrammatic representation of the various components of the system of which the electrophoresis device 10 is the central element. The electrophoresis device 10 has a gel module 24 with a cover 12 which houses a photometer 14 providing the separable photometer module 26. Used in conjunction with the gel module 24 are removable buffer wells 16 and 18 and removable electrode holders 20 and 22.

The gels for the electrophoresis may be formed in gel plate 100 using gel mold 102 having a top plate 104 and a lower plate 106.

A light box 200 is optionally provided for reading gels in conjunction with the photometer module 26, which can fit over the light box 200.

Signals from the gel module 24 and the photometer module 26 may be fed to a computer and data storage device 300, fitted with keyboard 302, CRT 304 and printer 306. By providing for an interactive relationship between the computer and data storage device, the gel module 24 and the photometer module 26, one can monitor the course of the electrophoresis and vary or maintain conditions as desired.

Figure 2:
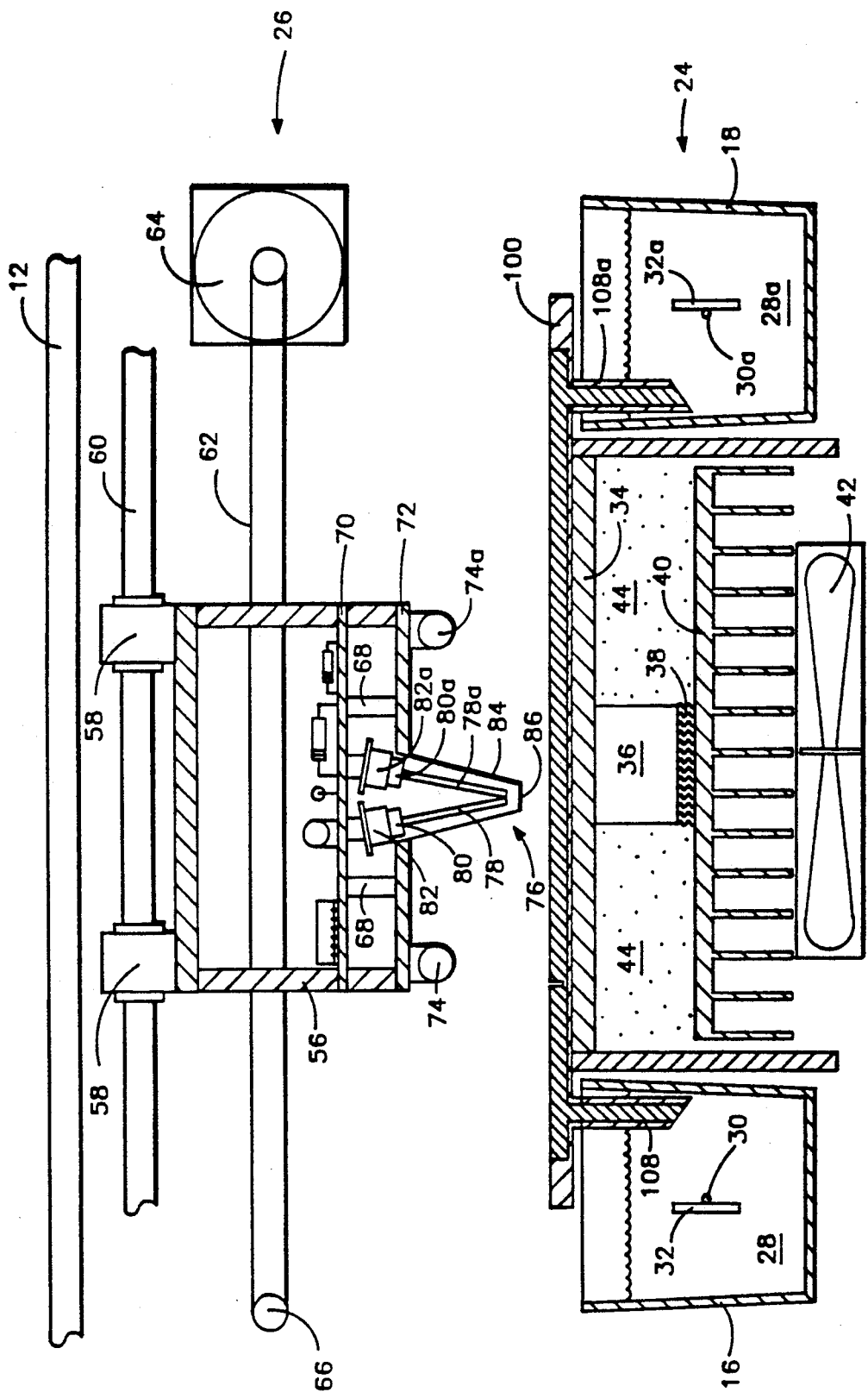
FIG. 2 is a diagrammatic sectional elevational view of the gel module.

In FIG. 2 the gel and spectrophotometer modules are depicted, where the gel module 24 is the lower component and the photometer 26 is the upper component.

The gel module 24 will have a first buffer solution well 16 containing buffer solution 28, electrode 30 and detachable electrode support 32. Similarly, buffer well 18 will include buffer 28a, electrode 30a and detachable electrode support 32a. The electrode support may be selected to interact with a detector to allow for continuous monitoring of the ionic levels of the buffer solutions. Thus, when the buffer solution 28 drops below a predetermined level of ionic strength, a pump, not shown, can be activated to replenish the buffer to a predetermined ionic strength by adding a concentrated solution. Various ion responsive electrodes may be employed for monitoring buffer concentration. In this way, the buffer may be maintained so as to avoid any interruption of the electrophoresis as a result of depletion of the buffer below a predetermined level.

The gel module 24 has a temperature control system comprising a thermal stage 34 mounted on a heat transfer block 36, which is in turn in heat transfer relationship with a thermal device, e.g., a Peltier device 38. The heat produced by the thermal device is transferred to the atmosphere by means of a finned heat sink device 40 and fan 42. The heat transfer block 36 and thermal device 38 are surrounded by insulation 44, where the various components of the temperature control system are housed within housing 46. The buffer wells 16 and 18 and the temperature control system 48 are supported by platform 50 of electrical circuitry housing 52.

Gel plate 100 is seated on copper thermal stage 34 and has legs 108 and 108a extending into buffer solutions 28 and 28a respectively.

The photometer module 26 comprises gel module cover 12 and photometer 14, as shown in FIG. 1. The photometer module has recessed well 54 for withdrawing the carriage 56 to inhibit any interaction between the gel plate 100 and the photometer 14. Carriage 56 is mounted on linear rod bearings 58 which ride on guide rod 60. Movement of the carriage is controlled by belt 62 which is driven by stepping motor 64, where the belt passes over idle pulley 66. By knowing the position from which the carriage initiated, one can count the steps of the stepping motor to determine the carriage position at any time. Alternatively, the stepping motor 64 may be connected to a monitoring device, e.g., a potentiometer, so that the location of the photometer 14 in relation to the gel can be monitored and the location of the bands in the gel determined. Supports 68 support circuit board, 70, and in turn are supported by floor 72 of carriage 56.

A blacklight bulb 74 serves as a light source for activating fluorescent components in the gel. A second black light bulb 74a may be employed to insure sufficient light intensity across the region absorbed by light sensing unit 76.

Light sensing unit 76 has two fiber optic pipes 78 and 78a. The fiber optic pipes 78 and 78a feed light from the gel to color filter disks 80 and 80a respectively. Individual fiber optic pipe pairs are provided for each lane to be observed, where the pipes may be to the same or different photodetectors. Means may be provided for individually sampling each pair of pipes. The color filter disks 80 and 80a have wave length absorption ranges of about 400–600 nm and 500–700 nm, where the transmission increases at higher wavelengths for the former and decreases for the latter. By appropriate Fourier analysis of the differences in the light absorbed and detected by photodetectors 82 and 82a respectively, one can measure the light at various wave lengths within a relatively narrow range of about 400 nm to 700 nm. The Fourier analysis is done by overlay of the transformed polynomial derived according to the absorption profiles of the two filters used in the separate detector channels. Thus, using discs from plastic or glass filter sheets, a color discrimination resolution of 50 nm is achieved.

As described, by having only two photodetectors and two filters, one can detect fluorescence or absorbence at different wave length ranges over a broad spectrum of visible light. A conical or triangular cross-section enclosure 84 encloses the fiber optic pipes 78 so as to direct light to the fiber optic pipes 78 through aperture 86. The carriage 56 can move the enclosure 84 with aperture 86 across the gel plate 100, where the blacklight bulbs will photoactivate fluorescent compounds present in the gel.

By employing light sources having broad wave length spectra which encompass the absorption maximum of fluorescers present in the gel, where the fluorescence occurs in relation to the movement of sample components in the gel, the component bands will fluoresce and the fluorescence will be detected by the photodetectors 82 and 82a. Where different components may provide for different fluorescent wave lengths, the ability to detect the presence of the different wave lengths allows for a determination of how far each component has progressed.

The photometer may be maintained in a single position, so as to detect the arrival or passage of one or more components past the position of the photometer, or may be repeatedly traversed across the gel plate, so as to repetitively monitor the progress of the electrophoresis.

The thermal stage 34 may be coated with a reflective material or a dark material, depending upon whether it is desired to reflect light from the gel or to absorb any light directed toward the cooling stage 34. A light reflective background provides greater levels of excitation. The choice will depend upon such considerations as the Stokes shift of the fluorescer present in the gel, the nature of the fluorescer, for example, where there is a significant time lag between absorption and electron excitation and fluorescence, the specific wave length of the excitation light and the fluorescent light, the fluorescence efficiency, and the like.

Figures 1, 9A:
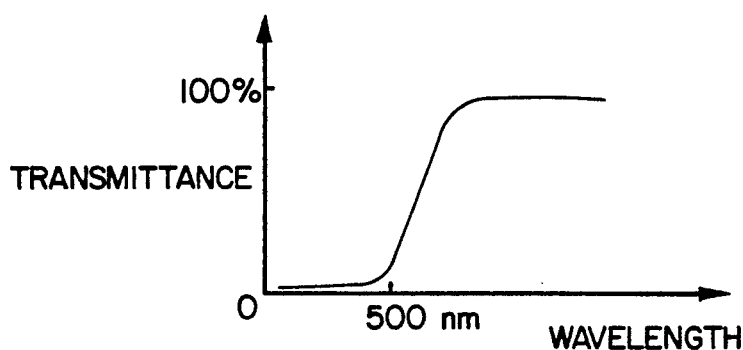
Figures 2, 9A:
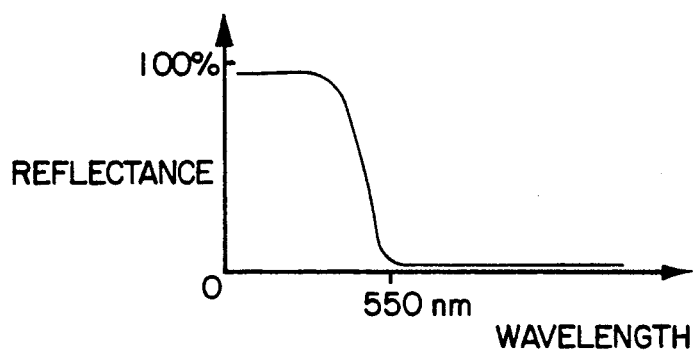
Figure 9:
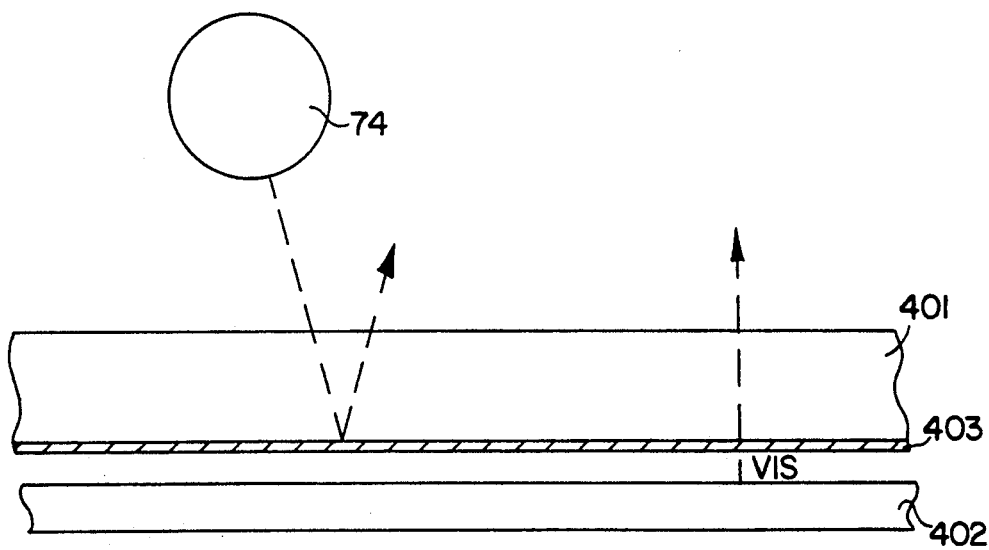

Visualization of the progress of sample components in the gel will be monitored by UV and visible light, as depicted in FIG. 9. The optical stage 401 mountable over the thermal stage 34 is coated or treated on one side with a spectral coating 403; in this case, the thermal stage will not be coated. The coating of the optical stage 403 is substantially transparent to visible light, transmitted from below the gel via a visible light source 402. The coating 403 is also reflective of UV light, preferably transmitted from above the optical stage 401 by a UV light source 74.

FIGS. 9a1 and 9a2 shows a graphic representation of the transmittance and reflectance characteristics of a presently preferred spectral coating. Thus, the presently preferred spectral coating for the optical stage transmits light above about 500 nm and reflects light below about 550 nm. Using this spectral coating, UV light and the lower wavelengths of visible light are reflected back toward the light source in the preferred arrangement of light source to gel. As a result, any dye in the gel or running with the sample in the gel will not be visible if it absorbs only at these wavelengths. Thus, dyes and other visualization materials must absorb at wavelengths above about 500-550 nm or a light source above the gel plate must be used, if visualization of the bands with visible light is anticipated.

Figure 4:
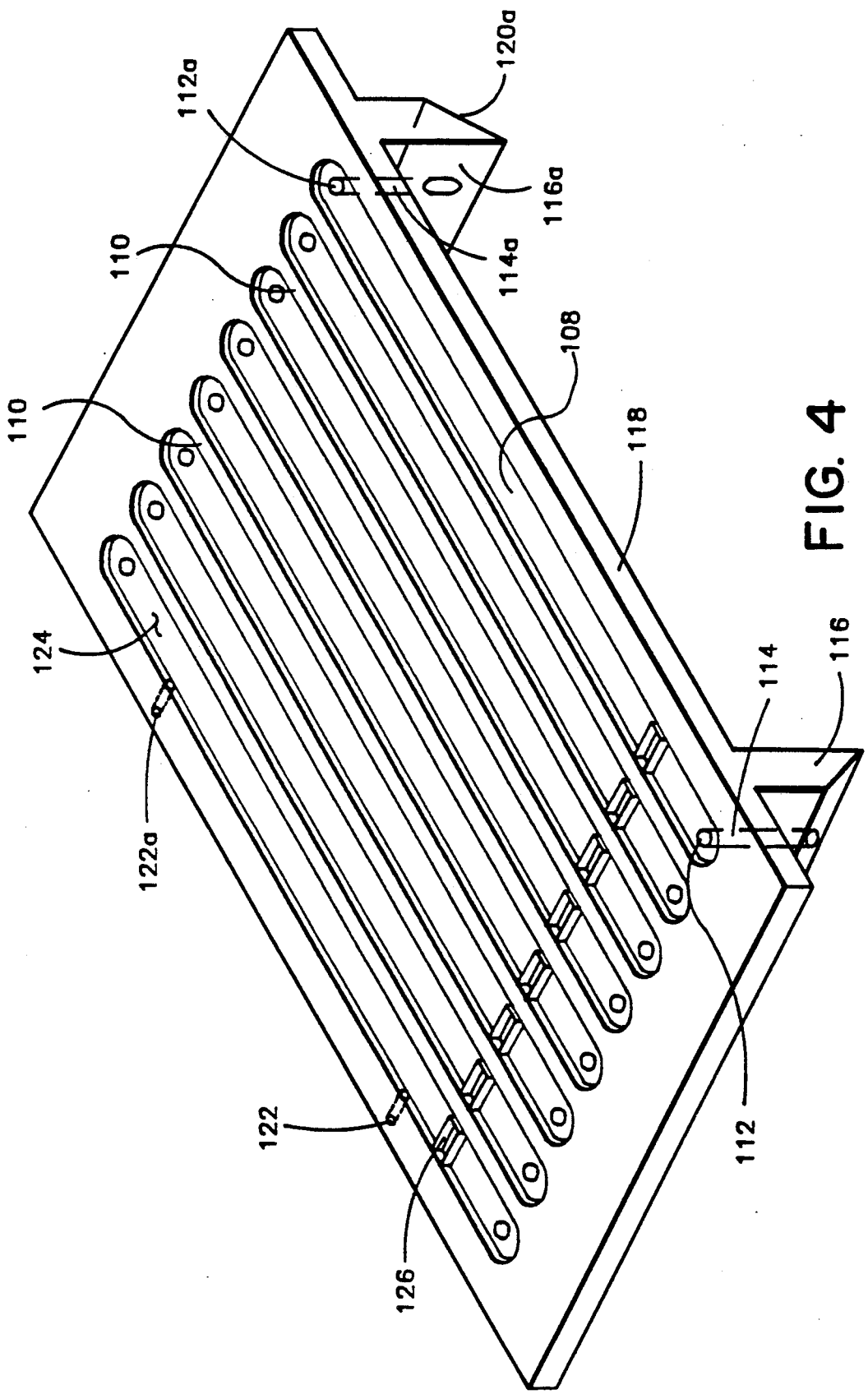
FIG. 4 is a perspective view of a gel plate according to this invention.
Figure 5:
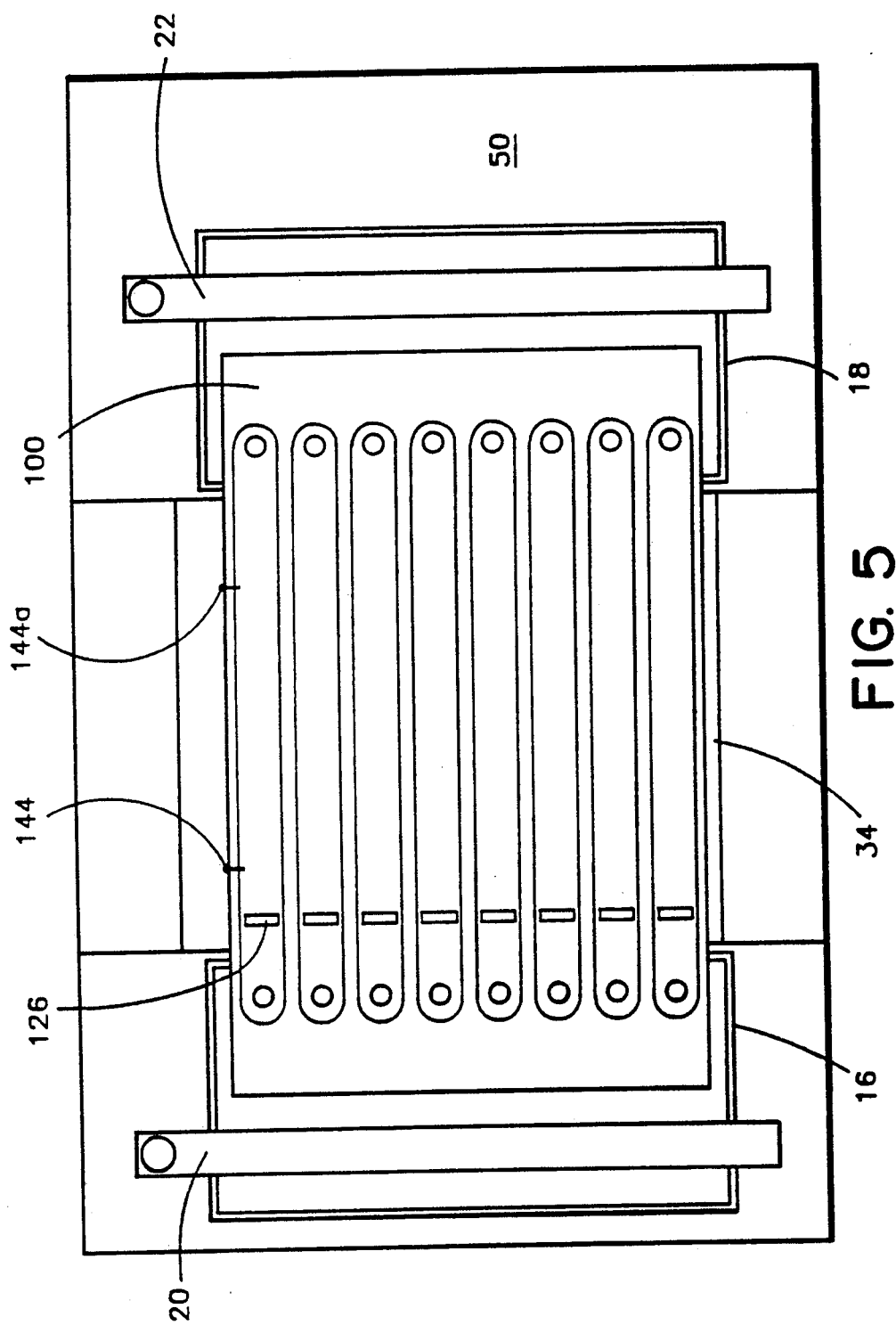
FIG. 5 is a plan view of the gel plate in the gel module.

In accordance with the subject invention, gel plates are designed for use with the gel module. The gel plate 100 is depicted in FIGS. 3a, 4 and 5, where FIG. 3 illustrates the gel mold in its opened and closed forms. The gel mold 102 has a bottom plate 104 which is desirably made of transparent plastic, so that one can observe the gel plate 100 for air bubble entrapment and also to allow for transmission of light.

The gel plate 100 has a plurality of lanes 108 separated by dividers 110. Proximal to each end of lanes 108 are orifices 112 and 112a which communicate with channels 114 and 114a, respectively. The channels may conveniently be produced in vertical support means 116 and 116a, fixedly attached in registry with the lanes to upper plate 118 which comprises the lanes 108. The channels 114 and 114a are in register with orifices 112 and 112a, respectively. The bottom of the vertical support means 116 and 116a have a beveled bottom 120 and 120a at an acute angle. The beveled bottoms protect the gel from contaminating surfaces, minimize air bubble blockage at the interface with buffer, and maximize gel and buffer interface.

The upper surface of plate 118 will normally be a clear plastic, where the bottom of the plate may be mirrored or blackened or left clear, allowing for thermal stage 34 or optical stage 401 to provide the appropriate light absorption or reflection characteristics.

Electrode receiving channels 122 and 122a are provided for introduction of electrodes which contact gel 124 in the first lane to monitor the electrical field gradient between 122 and 122a. Normally, the gel lanes will be cast from the same material, so that the field in the first lane will be substantially the same in each of the other lanes 108. For the most part, the fields will be dependent upon the ionic moieties present, which may or may not be affected by the differences in gel concentration in the different lanes. A sample well 126 is formed when casting the gel in the gel mold 102, although use of the sample applicator eliminates the need for sample wells.

The gel plate may be of any convenient size, generally ranging from about 5 to 40 cm in the direction of migration and about 1 to 20 cm normal to the direction of migration, particularly 7.5-15 cm by 12-15 cm. The channels 114 and 114a which communicate with the buffer and the gel will generally have a length of about 0.5 to 3 cm. Conveniently, the angle of the beveled bottom 120 and 120a will generally be from about 20° to 70°.

In FIGS. 3a and 4, the gel plate 100 is set onto gel mold lower plate 104, where vertical support means 116 and 116a fit onto slots 128 and 128a. At least one of the slots 120 and 120a extend all the way through the plate, so as to leave an opening, exposing the beveled bottom 120 or 120a to the atmosphere. Usually, both slots 120 and 120a are completely opened prior to introducing gel plate 100 onto gel mold lower plate 104. Lower plate 104 has four pins 130 for registering upper plate 106 in appropriate position in relation to gel plate 100.

Upper plate 106 has a plurality of protrusions 132 which extend into lanes 108 proximal to one end of the lanes to define the sample wells 126. The protrusions are of a size so as to extend not more than about 80% of the thickness of the gel and leave spaces, generally from about 1-2 mm between the dividers 110 and the protrusions 132. With gel at the bottom of the wells, the sample does not leak out of the wells. The spacing allows for air to pass when preparing the gel, thus avoiding air bubble entrapment. Usually, the space between the bottom of the well 126 and the plate 118 will be about 0.5 k mm.

In preparing the gels, the gel plate 100 is placed on gel mold lower plate 104, so that the channels 114 and 114a extend down into slots 128 and 128a. The top plate 106, which is conveniently of a semi-hard elastomeric plastic material has four recesses 134 for receiving pins or dowels 130. The top plate 106 is fitted over the lower plate 104 with the recesses 134 in register with the dowels 130 and the protrusions 132 extending into the lanes 108. The bottom 104 and top 106 plates are then locked together, so that the top plate face 136 is in contact with dividers 110, preventing gel from one lane to extend into a second lane. After locking bottom and top plates, 104 and 106 respectively, together with clamps, clips or the like, the plates are then set in a vertical position as shown in FIG. 3b. The lanes may then be filled either from the bottom or top.

When filling from the bottom, a manifold 138 is employed having tubes 140 which fit in register with channels 114. At the top of the manifold block are funnels 142, which connect with tubes 140, so that the gel may be introduced into the funnels 142, flow downwardly through tubes 140 into channels 114 and then flow upwardly to fill channels 114a up to or below the level in the manifold 138 to fill the channel and complete the gel. Polymerization of the gel may then be achieved by any convenient activation, such as light, heat, incubation under ambient conditions, or the like, where the course of the polymerization may be monitored by the temperature profile using a temperature sensor, not shown, change in appearance, or the like.

When filling the lanes 108 from above, one can provide for a manifold which can be placed in register with the channels 114a and provide for a porous cover over channels 114, which will allow for air to pass, but prevent passage of the liquid gel. By first filling one row of channels 114 with the gel, the gel may then be added from above without an entrapment.

Other techniques may also be used for producing the gels. In some instances, it may be desirable to provide for various gradients in the gel, providing for areas having different concentrations (%T; where T=total amount of acrylamide or other gelling agent) and different hardnesses.

For example, an improvement over currently used gels is seen wherein a stacking gel is formed in the column 114 of the vertical support means (or blocks) 116 ending at the level where the vertical support 116 meets the gel plate 118, or ends further into the gel plate, close to or beyond the region of the sample wells 126. Alternatively, the portion of the gel immediately downstream from the sample well may comprise a stacking gel, which will have a lower percentage of polymer followed by the separation gel.

By adding different substantially immiscible liquids sequentially, one may obtain a stepped gel having regions of different characteristics. One can also vary the gel hardness by employing staged cure times for the different regions.

The stacking buffer gel is poured in the leg of the tray, in the gel channels 114, using a gel of specific ion composition and content. The ionic content is chosen so that the lead ions of the stacking gel migrate more quickly through the stacking gel than the buffer ions associated with the separating gel. When the faster-migrating ions of this stacking gel reach the sample zone, the differential in ion migration rates causes a sharpening of the sample band. For enhanced visualization of this sharpening, a dye may be added to the stacking buffer gel which will allow visual and photometer monitoring of the process.

When the gel is formed, the gel plate 100 may then be placed upon the thermal stage 34 or optionally upon the optical stage 401 with the vertical support means 116 and 116a immersed in wells 16 and 18 respectively. Electrodes 144 and 144a are introduced through apertures in a side wall into electrode receiving channels 122 and 122a respectively for monitoring the electrical field of the gel in lane 1. Electrode holders 20 and 22 are placed in buffer wells 16 and 18 to provide for the electrical field across the gel. In an improved gel system, a sample applicator assembly is also provided. FIG. 10 is a sectional view of the sample applicator 407 preferably formed of a transparent material to simplify the loading and monitoring of sample. The sample is loaded into a application channel 404 which is preferably round or oblong in shape. At the bottom of each channel is a wick 405 attached to the bottom of the applicator 407 by heat fusion 408, adhesive or the like. In a typical use, a pipet tip 406 will be used to introduce the sample into the application channel 404. A full perspective view is depicted in FIG. 10a.

The wick 405 is selected to hold a measured amount of sample, and thus the sample may be applied slowly and evenly to the gel when the wick is contacted with the gel 124 and a current is applied.

Figure 6:
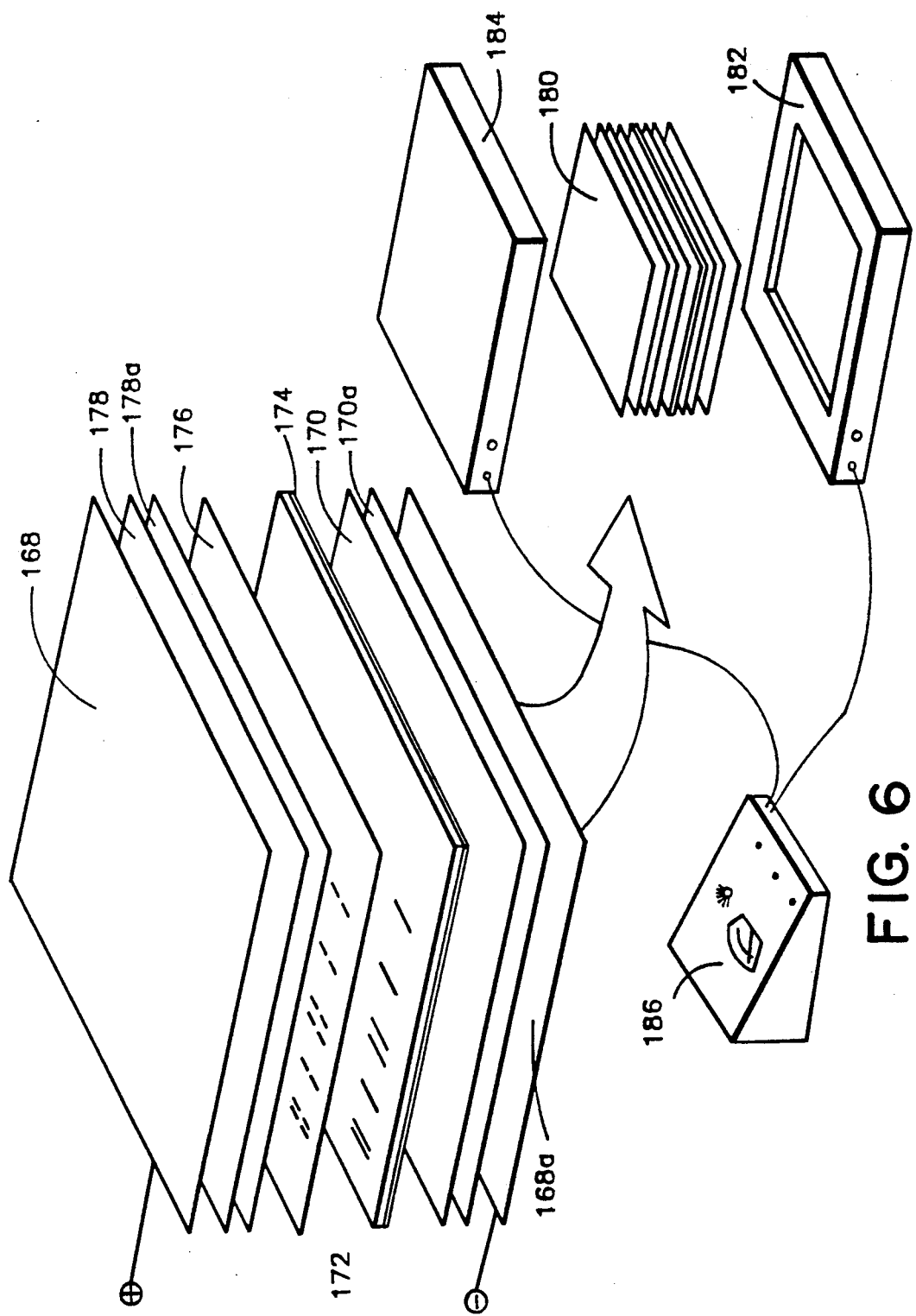
FIG. 6 is a perspective view of components for blotting the gel.

At completion of the electrophoresis, the band components may be transferred from the gel to a membrane or other conventional substrate, employing the equipment depicted in FIG. 6 for the transfer. A stack of sheets are employed having a graphite electrode sheet anode 168 and graphite electrode sheet cathode 168a. Placed above the graphite cathode 168a are paper sheets 170 and 170a soaked with buffer solution. The gel 172 is supported by Netfix substrate 174 for transfer of the bands to a permanent record. For receiving the gel components, membrane 176 is placed in contact with gel 172. Any convenient membrane may be employed, such as Immobilon, nitrocellulose, DBM-nitrocellulose, etc. Above the membrane are placed paper sheets 178 and 178a, which are also soaked with buffer solution. The paper sheets 170, 170a, 178 and 178a allow for transfer of current between the electrodes 168 and 168a.

The package of sheets 180 is placed into a lower electrode frame 182 and then enclosed with upper electrode frame 184. The electrode frames 182 and 184 are connected to a power supply 186, which may also include a timer.

The current is maintained for a sufficient time for transfer of the separated components in the gel to the membrane for further processing and analysis.

Figure 11A:
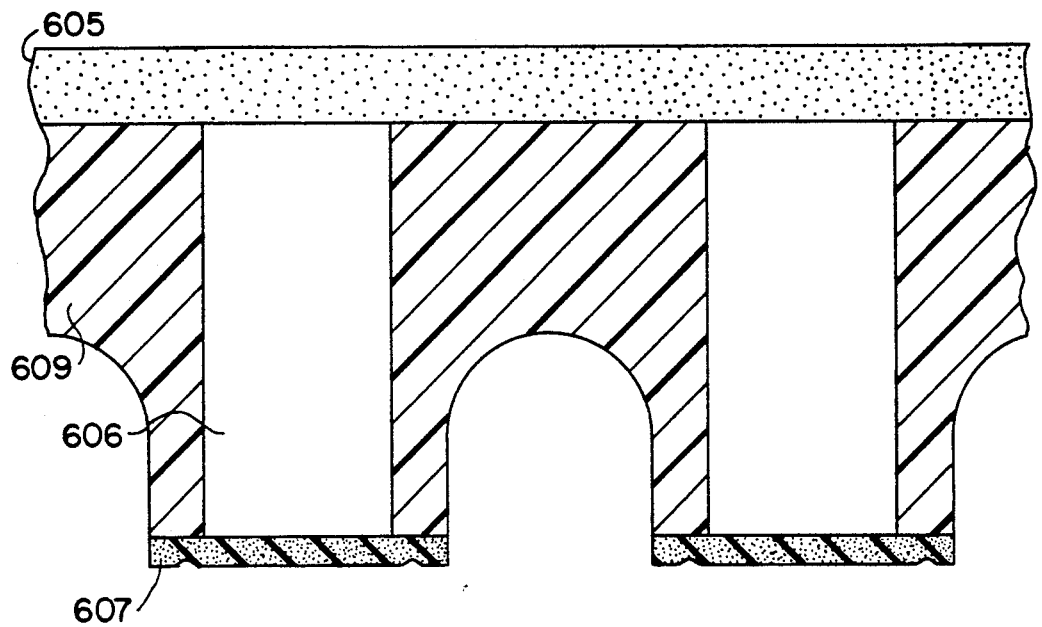
FIGS. 11a and 11b are a perspective view of the sample retriever, with a cross-section to show the preferred relationship of graphite electrode, electroconductive media matrix, and wick and the preferred elliptic shape of the base of the retrieval channel.
Figure 11B:
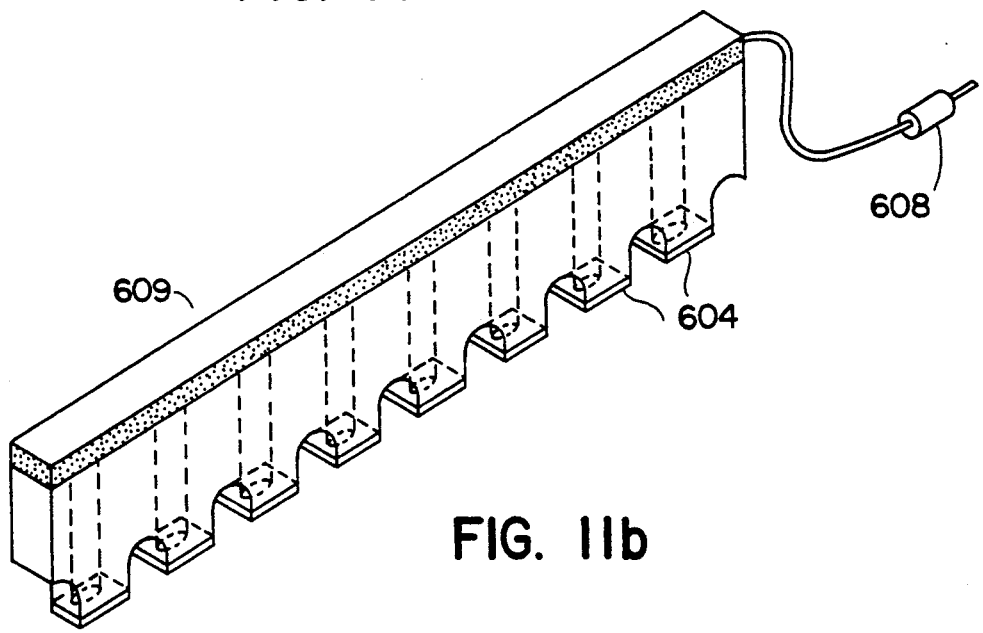

Alternatively, an individual portion of the sample, all or part of a band or bands, is removed from the gel by a sample retrieval device. A presently preferred embodiment is depicted in FIG. 11. The gel retriever 609 is similar in design to the sample applicator, with several important modifications. The basic structure of the retriever is a piece of preferably transparent material 609 with columnar channels 604, opening at the top and bottom of the retriever. The channels are effectively closed at the bottom by a wick 607, and the channels are preferably oblong in shape at the openings 604, which prevents the formation of air bubbles in the channels. At the top of the retriever, a graphite electrode 605 is contactable with electroconductive media in the channels. In the channels, a matrix material 606 holds buffer in the channels, which would otherwise run out through the wick onto the surface of the gel.

The retriever operates by placing a wick attached to the retriever in contact with the surface of the gel 126 above a band to be retrieved, and establishing a current flow between the graphite electrode 605 and one other electrode so that current flows through the gel, through the wick, into the electroconductive media matrix 606 toward the graphite electrode. This draws the sample to be retrieved into the matrix 606, from where it may easily be recovered without the necessity for disrupting the gel material. The sample may be reapplied on the same gel or another gel or media by reversing the field. The retriever is readily adapted for use with isoelectric focusing gels, two-dimensional gel papers, and other types of separating methods where a current can be used to move sample from a solid support into the retriever.

A diluter-dispenser device can be provided as a container, for diluting buffer concentrate or other solution to a desired concentration.

Figure 7:
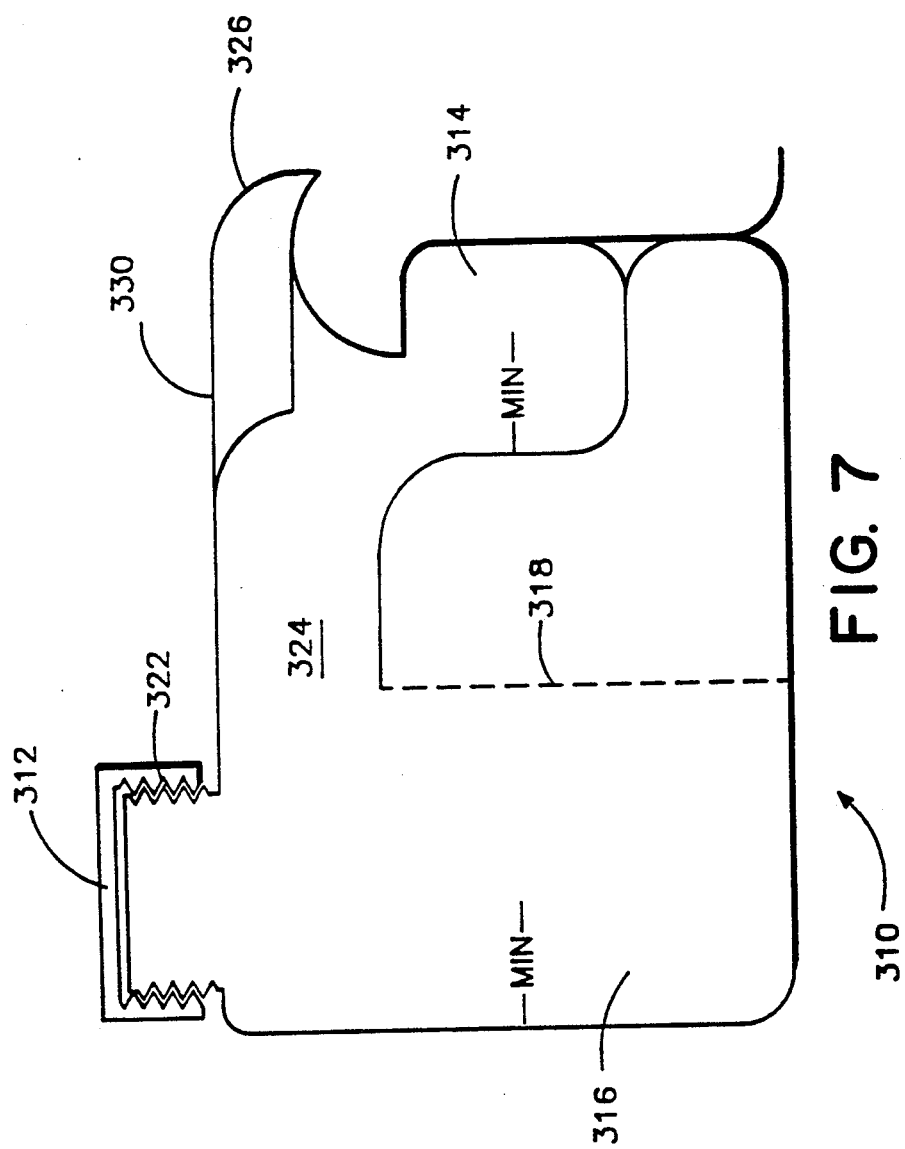
FIG. 7 is a cross-sectional elevational view of a mixing device.
Figure 8:
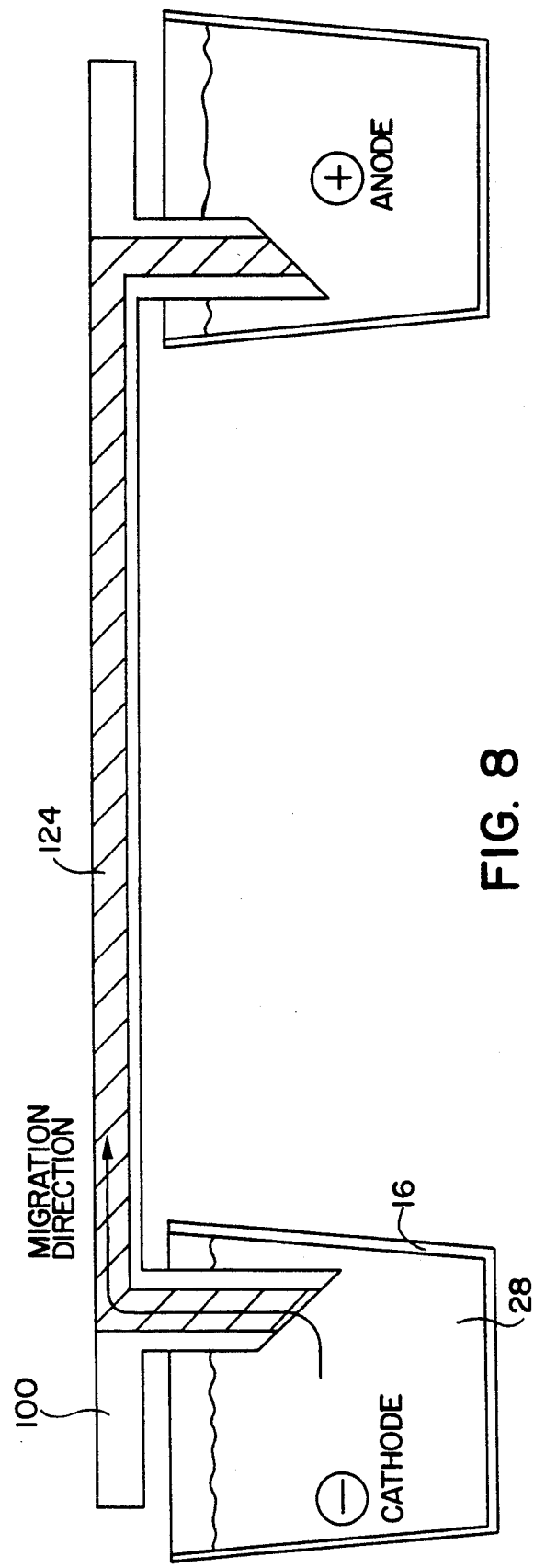
FIG. 8 is a perspective view of the gel plate with legs accommodating a stacking buffer gel.

The diluter-dispenser device 310 shown in FIG. 7 is conveniently made as a molded one-piece device with a separate cap 312. The device has a small chamber 314 for receiving the buffer concentrate. A large chamber 316 receives water or other liquid for diluting the concentrate. The diluent is poured into chamber 316 to a predetermined level which is below the top of well 318. The concentrated buffer may then be poured through opening 320 to fill chamber 314 to a designated level. Cap 312 may now be screwed on to threaded channel 322 and the device 310 tipped so as to transfer the concentrated buffer from chamber 314 to the diluent in chamber 316 where it may be mixed by shaking. Once the buffer has been appropriately diluted, it may now be poured from chamber 316 through channel 324 and out pour spout 326.

Having described the various components of the subject system, the use of the system and its various applications will now be considered.

Various gel compositions may be employed to produce the gel matrix. Polyacrylamide, agarose, gelatin, or other agent may be used as a thickening agent for the gel matrix. The gel plate 100 with its plurality of lanes is placed over the lower plate 106 of the gel mold and the channel blocks 108 and 108a seated in slots 128 and 128a. The cover 104 is then placed over the gel plate 100 with the dowels 130 of the lower plate in the recesses 134 and the lower plate 106 and upper plate 104 of the mold held together by clips. The manifold 138 is then placed against the lower plate 104 with the plurality of tubes 140 in register with the channels 114. Suction may be used to pull the gel into the lanes. The components are mixed to form the gel matrix, either at an elevated temperature to lower the viscosity or containing unpolymerized monomer. This composition is then poured into the manifold 38 so as to travel through the lanes 108 and up and out channels 114a. Where the solution has been heated to obtain the desired low viscosity, the solution will be cooled and allowed to gel.

For the most part, with polyacrylamide, the solution will include a chemical or photoinitiator system. Various chemical polymerization systems may be used which are added to the matrix before preparing the plate. For example, TEMED and persulfate may be added to provide polymerization initiation. With the photoinitiator system, the gel composition will be irradiated with light to provide the necessary excitation for polymer initiation and the course of the polymerization followed by employing a thermocouple. Once the temperature becomes stable or approaches ambient temperature, the polymerization may be assumed to be complete. If desired, an acrylamide gradient may be developed by successively adding solutions with increasing amounts of acrylamide and/or cross-linking agent. Alternatively, differential initiation may be used, so as to provide varying degrees of polymerization. In this manner, one may provide for a gel gradient.

In standard Polyacrylamide Gel Electrophoresis (PAGE) technology, gels commonly range between 5-22.5% T (T =total amount of acrylamide or other gelling agent), mostly between 5-15% T. Lower percentages may be employed with linear polymerized acrylamide. In agarose gel electrophoresis, concentrations between about 0.2-2% T may be employed.

Also, one may provide for a region which is referred to as the stacking gel, having a relatively low gel concentration (wide pore size) and a resolving gel (separation gel) having a substantially higher gel concentration (narrow pore size). Descriptions of forming gels for gel electrophoresis may be found in *The Practice of Quantitative Gel Electrophoresis*, cited above. Because of the ability to regulate and monitor the course of the electrophoresis, low concentrations of the gelling agent may be employed.

Depending upon the purpose of the electrophoresis, various buffers may be employed at different pHs, where the gel and the buffers in the buffer wells may conveniently have a common ion. Other components in the gel may include cross linking agents such as BIS, DATD, AcrylAide, etc. Once the gel has been formed filling the lanes and extending through the channels, the mold may be opened and the gel plate released, which is now ready for use.

The buffer wells 16 and 18 are positioned appropriately adjacent to the gel module platform and the gel plate is placed over the gel module with vertical support means extending into the buffer solution in the buffer wells. The electrode holders containing the electrodes are then placed into the buffer solutions to provide the anode and cathode for the anolyte and catholyte solutions to direct the flow of ions and charged sample components. The sensing electrodes are inserted into the holders and extend into the gel, upon positioning the gel plate on the gel module platform. The sensing electrodes are internally connected to the computer.

The sample may now be introduced into the gel either via sample wells or with the sample applicator.

The sample applicator assembly provided in this invention automatically applies an even, consistent portion of sample to the gel, and is adaptable to the automated gel electrophoresis assembly so that sample may be loaded automatically at a predesignated time. The applicator consists of a housing of plastic or other material, with applicator channels through which sample may be introduced into the applicator, by pipet tips which conveniently fit into the applicator channels or by other means. After sample has been introduced into the channels, the applicator may be positioned on the gel. An applicator channel will be in register with a lane of the gel. The applicator may be automatically removed from the gel surface after completion of sample entry.

As the electrophoresis proceeds, the temperature and voltage in the gel is continuously monitored. If the electrophoresis is moving too slowly, the field, e.g, the voltage gradient, may be increased in the gel. Thus, the progress of the electrophoresis is monitored and the progress of the bands slowed or speeded, depending on the satisfactory nature of the separation.

Internal markers may be included in the sample or in control lanes. Derivatives of compounds may be employed, which are fluorescent or absorbent, which may include proteins, nucleic acids, saccharides or particles. Where one is looking for a known compound, the marker conjugated compound may be used in a control lane.

The photometer can be continuously moved across the gel, moving back and forth with a particular frequency, may occasionally move across the gel, or may be directed to move at particular time intervals. Fluorescence can be provided by using fluorescent standards in a control lane, by providing for fluorescent compounds which bind to the sample components, by providing for compounds in the gel which interact with the sample components to provide fluorescence, or the like. In this manner, the various bands which form in the gel can be monitored, so that the progress of the leading band and the separation between bands can be detected. Conditions can be changed to enhance separation or to stop the electrophoresis, when a desired degree of separation has been achieved.

The optical stage assembly provided in this application enhances the sensitivity of the photometer readings and combines them into one assembly. Three modes of illumination are provided with this assembly: ultraviolet induced fluorescence, visible light absorption and a combination of the two.

The spectral coating reflects ultraviolet light to maximize the illumination of the sample in the gel plate for fluorescence readings. The spectral coating transmits visible light so that, for example, an illuminating back panel containing a visible light source can be used for absorption measurements of dyed samples. Additionally, both illumination modes can be used simultaneously, to take advantage of a broader light range and allow for better discrimination of bands, for example, where samples might be emissive and markers absorptive.

A primary advantage of this design is that all modes are utilized in the same assembly, which reduces handling of the gels and allows for a more efficient heat-transfer assembly for cooling and heating of the gels.

The various signals obtained from the gel module and photometer module are fed to a computer, which interacts with the temperature control and electrodes which provide the voltage gradient and sense the voltage gradient in the gel. A keyboard is provided which interacts with the computer so that the variables may be changed in accordance with the performance of the electrophoresis and the desires of the operator.

Conditions of the electrophoresis may be monitored with a CRT and hard copies of the conditions and band separations may be made with a printer connected to the computer. By employing lanes having different levels of thickener or polymer, Ferguson plots may be developed which are characteristic for a particular compound, e.g, protein, (characterization in respect to size and charge). Alternatively, Ferguson plots may be developed from a series of homogeneous gel runs of different concentrations by combination of the respective data files.

A program is provided which relates the various signals obtained from the gel module and the photometer module to the course of the electrophoresis and maintains constant conditions in the gel as to temperature and electrical gradient by modifying the voltage at the electrodes in the buffer wells and the rate of cooling or heating provided by the thermal system.

A diluter-dispenser is provided for diluting buffer concentrate or other reagent, which can be provided as part of the system. A small cup is provided which is filled to a predetermined level, while a mixing container connected to the cup is filled with water or other solution to a predetermined level. By tilting the diluter-dispenser, the concentrate in the cup is transferred to the mixing vessel, where it is diluted and may then be dispensed through the connecting channel in a pour spout into the buffer wells.

Once the electrophoresis is complete, the gels may then be used in a variety of ways. For nucleic acids, various dyes, such as ethidium bromide which intercalates into nucleic acids and is fluorescent, may be employed. After washing away ethidium bromide which is not intercalated, the photometer may be used for detecting the fluorescent bands. Alternatively, a dye in the visible range may be used, e.g., Coomassie blue, and the gel plate may be moved to the light box for viewing the visible bands. If the dye is fluorescent, the photometer module may be removed from the gel module and placed over the light box. The photometer module will feed the fluorescent signals which are observed to the computer. The electroluminescent panel may be employed to detect a dye absorbing in the visible range.

While the gels may be analyzed directly, in many situations, one may wish to transfer the separated molecules from the gel onto a membrane. For this, one removes the gels from the lanes onto a porous substrate, such as Netfix, or the like. A stack of sheets are provided, where the gels are sandwiched between papers wetted with buffer, which are in turn sandwiched between sheet electrodes. By introducing an electrode frame attached to a power supply, the components in the gel may be transferred to the membrane and covalently or non-covalently bonded to the membrane. The sample components may then be probed, with antibodies, nucleic acid probes, or the like.

The subject system may be used not only for electrophoresis, but also for isoelectric focusing in carrier ampholyte or immobilized pH gradient gels. Steady-state conditions may be monitored directly using fluorescent propidium iodide markers.

The system requires only a small power supply, for example, providing 0–500V at currents of 0–50 milliamps, usually providing independent regulation of voltage and current. The thermal system has a capacity to remove or add heat at a rate of about 0–45 W with a precision of about $\pm 0.1°$ C.

The system can be used for detecting and characterizing a wide variety of sample components. The system may be used to monitor food, detect viruses, diagnose diseases (such as the production of isozymes as occurs in myocardial infarction, typing, as to major histocompatibility complex antigens, blood type, or the like), detect sugars, lipid complexes, etc. For sugars, it may be convenient to form boronates, where the boron may be attached to a charged molecule, such as polyphosphate, polyacrylate, etc. The ability to carry out separation in a plurality of lanes under identical conditions allows for accurate determinations of components in a sample because of the reproducibility of the system.

It is evident from the above description, that a convenient total electrophoretic system is provided which allows the user to prepare his own gels or buy them preformed, carry out electrophoresis in an efficient and reproducible manner under controlled conditions and then use the gels in accordance with knob procedures for specifically determining the particular components of the sample. In addition, a stacking gel is provided separate from the gel plate, which allows for substantial concentration of the components of the sample, further improving the efficiency of separation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A gel electrophoresis system for separating components of a mixture by their physical and chemical characteristics by passage through a gel under a voltage gradient, said system comprising:
   a. a housing comprising a gel electrophoresis module, and electrical circuitry for external connection, sample applicator and retrieval means, and a gel plate;
   b. said gel electrophoresis module comprising a temperature control platform, a removable optical stage reflective for light in the ultraviolet range and transparent for light in the visible range, supported by said platform, buffer wells on opposite sides of said platform, power electrodes for creating a voltage gradient in said gel, and sensing electrodes for reading the voltage gradient for feedback to the power electrodes;
   c. a gel plate for mounting on said platform and supporting a gel, said gel plate comprising aligned orifices proximal to opposite ends of a horizontal gel support, and first and second vertical support means for extending into said buffer wells and comprising channels communicating with said orifices, a separation gel on said horizontal support and a stacking gel in said channels of said first vertical support, wherein said stacking gel and said separation gel abut at said orifices or on said horizontal gel support in the direction of migration;
   d. a sample applicator assembly for application of sample to said gel, said applicator assembly comprising a housing having at least one passageway, with an upper opening for receiving liquid sample and a lower opening covered with an absorbent material for absorbing said sample and delivering said sample to said gel; and
   e. a sample retriever assembly for removing portions of sample from said gel after at least partial separation, said retriever assembly comprising a housing having at least one passageway for receiving an electrically conductive medium, with an upper opening for withdrawing sample and a lower opening covered with an absorbent material to contact said gel over said portion, said electrically conductive medium in said passageway for electrical contact with said absorbent material; and an electrode positioned for contact with said medium.

2. A gel plate comprising:
   a flat horizontal support for a gel comprising aligned orifices at opposite ends of said support;
   a separation gel in a plurality of lanes recessed in said horizontal support; and vertical support means at opposite ends of said horizontal support, said vertical support means comprising aligned channels filled with a stacking gel in contact with said separation gel at said orifice or on said horizontal support.

3. A gel plate of claim 2, wherein said channels terminate in a beveled bottom at an acute angle, and wherein said horizontal support has a side wall with at least two spaced apart apertures for receiving sensing electrodes.

4. A sample application device comprising:
   a housing;
   at least one channel extending through said housing and having an upper sample receiving opening and a lower sample component dispensing opening;
   a gel in said channel extending from said lower opening at least a portion of the length of said channel; and
   an absorbent wick layer covering said lower opening and in contact with said gel.

5. A sample application device of claim 4, wherein said housing has a plurality of channels and wicks, with each wick separated from the other wicks.

6. A sample application device of claim 5, wherein said plurality of channels are spaced apart in relation to the spacing of lanes in a gel for electrophoresis.

7. A sample application device of claim 4, wherein said housing is transparent.

8. A sample application device of claim 4, wherein said wick is composed of spun fabric.

9. A sample retriever device comprising:
   a housing;
   at least one channel extending through said housing to provide upper and lower openings in said housing;
   material in said housing extending from said lower opening at least a portion of the length of said channel, said material absorbing or comprising an electrically conducting medium in said channel;
   an absorbent material wick covering said lower opening and in contact with said material; and
   an electrode in contact with said material distal from said lower opening.

10. A sample retriever of claim 9, comprising a plurality of channels, and wherein said electrode is formed of individually chargeable sections.

11. A sample retriever of claim 9, comprising a plurality of channels and wherein said electrode is a singly chargeable electrode.

12. A sample retriever of claim 9, comprising a plurality of channels, wherein said channels are spaced apart in relation to the spacing of lanes in a gel for electrophoresis.

13. A method for applying, separating, retrieving and reapplying a component of a sample from a gel, said method comprising;
   a. applying sample to be electrophoresed to a gel by means of a sample applicator, comprising a container which includes said sample and an absorbent wick in contact with said sample for contacting said gel, said applying comprising contacting said gel with said wick at a sample receiving site under the influence of an electrical field in said gel;
   b. applying current across said gel between first and second electrodes such that components of said sample migrate at different rates through said gel;
   c. identifying at least one individual component in said gel;
   d. applying an absorbent wick to said gel at said identified component, wherein said wick is in electrical communication with a retrieval electrode through an electrically conducting medium and covers only a small area including said component;
   e. passing a current through said retrieval electrode and an electrode in electrical communication with said gel and on the opposite side of said component from said retrieval electrode,
   whereby said component migrates from said gel into said electrically conducting medium and is available for reapplication to a gel.

14. A method of claim 13, wherein said electrically conducting medium is an absorbent material and an electrically conductive liquid.

15. A method of claim 13, wherein said component is fluorescent or is labeled with a fluorescent molecule and said identifying comprises:

irradiating said gel with UV light, wherein said UV light passes through said gel and is reflected back through said gel; and detecting the presence of fluorescence from a position of said gel as indicative of the presence of a component of said sample at said position.

16. A method of claim 13, wherein said component is light absorbent or is labeled with a light absorbent molecule, said method comprising:

irradiating a position of said gel with visible light on one side of said gel; and detecting the absorption of light at said position as indicative of the presence of said component of said sample at said position.

17. A method of separating temperature denaturable components in a sample, said method comprising:

transferring said sample to an electrophoresis gel at a sample receiving site at a temperature below denaturing of said components;

applying an electrical field to said gel while raising the temperature of said gel in accordance with a predetermined regimen; and identifying the position in said gel of said components in relation to the temperature at the time said component migrated to said position;

whereby said components are identified by their rate of migration and denaturation temperature.

18. A method of claim 17, wherein said electrophoresis gel is a soft gel.

19. A method of claim 17, wherein said temperature regimen is controlled by controlling the rate of cooling of said gel, wherein said gel is heated as a result of said electrical field.

20. A method of claim 17, wherein said components are proteins.

21. A method of claim 17, wherein said components are first partially separated by an electrical field at a fixed temperature below a denaturation temperature.

22. A kit comprising in combination, a sample applicator assembly for application of sample to said gel, said applicator assembly comprising a housing having at least one passageway, with an upper opening for receiving liquid sample and a lower opening covered with an absorbent material for absorbing said sample and delivering said sample to said gel; and a sample retriever assembly for removing portions of sample from said gel after at least partial separation, said retriever assembly comprising a housing having at least one passageway for receiving an electrically conductive medium, with an upper opening for withdrawing sample and a lower opening covered with an absorbent material to contact said gel over said portion, said electrically conductive medium in said passageway for electrical contact with said absorbent material; and an electrode positioned for contact with said medium.

23. A kit of claim 22, wherein said kit further comprises an optical plate having a coating reflective below about 500-550 nm and transmissive above about 500-550 nm.

24. A method for detecting the presence of a component of a sample, said method comprising:

(a) applying said sample to be electrophoresed to a gel;

(b) applying current across said gel between first and second electrodes such that components of said sample migrate at different rates through said gel;

(c) identifying the presence of at least one component in said gel;

(d) applying an absorbent wick to said gel at said identified component, wherein said wick is in electrical communication with the retrieval electrode through an electrically-conducting medium and covers only a small area including said component;

(e) passing a current through said retrieval electrode and an electrode in electrical communication with said gel and on the opposite side of said component from said retrieval electrode, whereby said component migrates from said gel into said electrically conducting medium.

25. A method according to claim 24, wherein said identified component in said electrically-conducting medim is further characterized.

26. A method according to claim 24, wherein said identified component is identified by means of fluorescence.

* * * * *